United States Patent [19]

Lerner et al.

[11] 4,111,049
[45] Sep. 5, 1978

[54] APPARATUS FOR SECURING VAPOR SAMPLES

[75] Inventors: Melvin Lerner, Bethesda, Md.; Richard A. Ericson, Shelton, Wash.

[73] Assignee: The United States of America as represented by the Commissioner, United States Customs Service, Washington, D.C.

[21] Appl. No.: 794,572

[22] Filed: May 6, 1977

[51] Int. Cl.² .............................................. G01N 1/22
[52] U.S. Cl. .............................................. 73/421.5 R
[58] Field of Search ............... 73/421.5 R, 52, 432, 73/23.1, 19

[56] References Cited

U.S. PATENT DOCUMENTS 3,805,593   4/1974   Sandoz et al. .......................... 73/41
3,998,101  12/1976   Bradshaw et al. ............. 73/421.5 R

FOREIGN PATENT DOCUMENTS 238,102  12/1963  Austria ........................................ 73/41

Primary Examiner—Donald O. Woodiel
Attorney, Agent, or Firm—Nina M. Lawrence; John R. Manning

[57] ABSTRACT

Apparatus is described for securing vapor samples, particularly from articles such as suitcases, travel bags, packages, and the like. The apparatus may include several depressor arms hinged above a station along a conveyor belt or the like. A sampling probe for sampling vapor expelled from the articles is positioned at the station. As the articles are carried by the conveyor past the station, they lift the arms which are suitably hinged above them so that the weight of the arms causes a part of the vapor accumulated in the article to be expelled. The expelled vapor is sampled by the probe at the station and may be carried to a suitable vapor analyzer for test.

13 Claims, 1 Drawing Figure

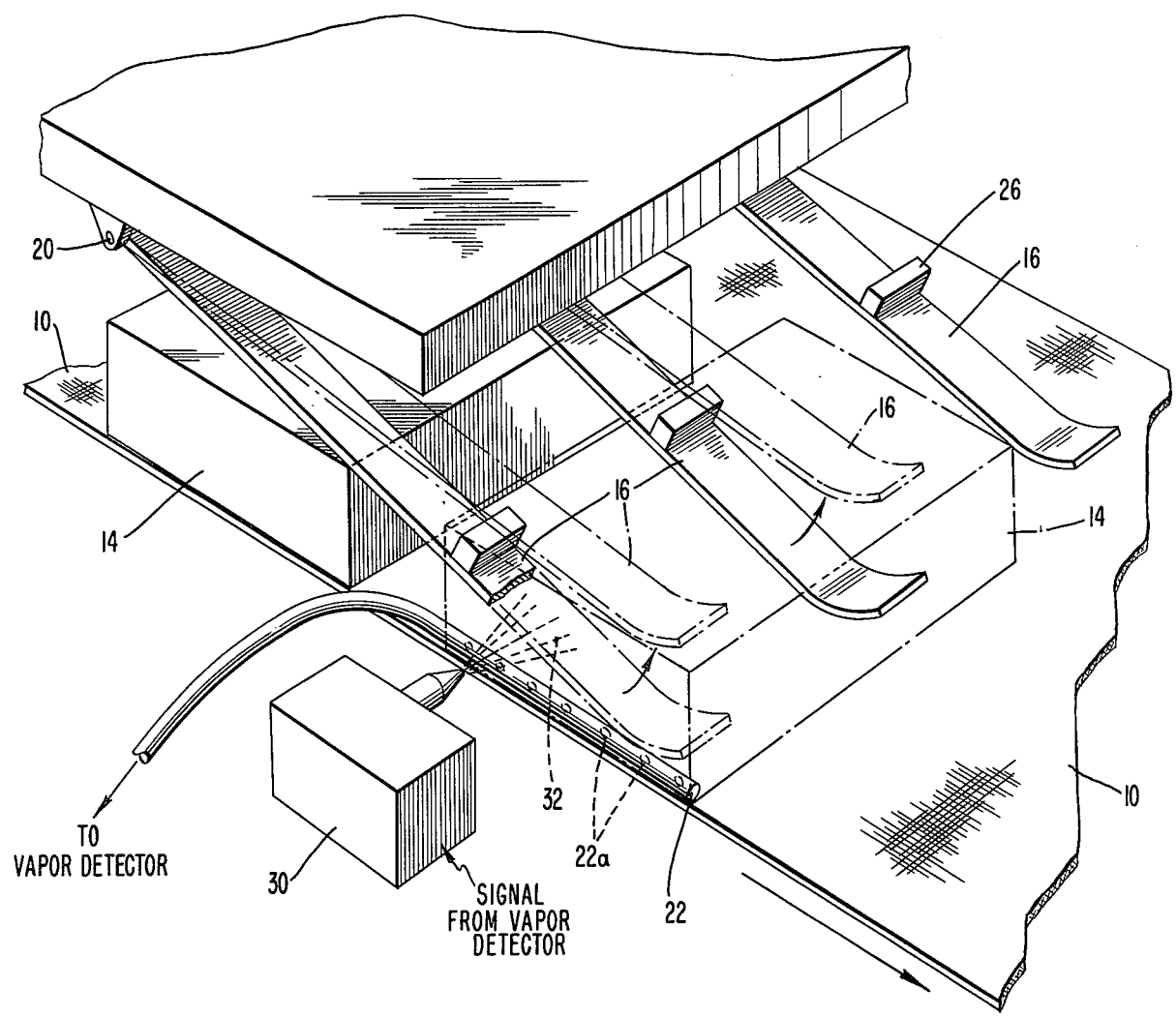

APPARATUS FOR SECURING VAPOR SAMPLES

The invention described herein was made by employees of the United States Government and may be manufactured and used by or for the Government for governmental purposes without the payment of any royalties thereon or therefor.

BACKGROUND OF THE INVENTION

The present invention relates to apparatus for securing from containers, such as packages, baggage, or other articles, vapors which may be analyzed. Apparatus for securing vapor samples for testing for various purposes is known. For example, in U.S. Pat. No. 3,942,357 to Jenkins, issued Mar. 9, 1976 is described an apparatus for checking the contents of closed containers for certain characteristic vapors. The Jenkins apparatus involves placing the containers or articles to be checked within a closed chamber which is evacuated in order to draw from the container the vapors to be checked. The articles in the closed container are subjected to vibration of the atmosphere within the chamber. Such vibration subjects the containers alternately to increased and decreased pressure, thereby tending to mix the vapors within the containers with the air in the chamber. The air in the chamber may then be sampled to secure a sample of the vapors thus secured from the containers. Other arrangements for testing often include chambers using evacuation. Means for testing may involve heating the container to expand and thereby cause the gas within to be expelled, if there is a leakage path, whereupon the expelled gas may be detected by a suitable vapor detector. Among patents which described techniques for detecting or obtaining vapor samples from containers are U.S. Pat. No. 3,918,293 issued to Feigel on Nov. 11, 1975; U.S. Pat. No. 3,757,587 issued to Ahnsorge on Sept. 11, 1973; U.S. Pat. No. 3,847,013 issued to Luy on Nov. 12, 1974; and U.S. Pat. No. 3,956,923 issued to Young etal. on May 18, 1976.

SUMMARY OF THE INVENTION

According to the present invention, at a conveyor station means are provided for exerting a force on the article under test. An especially simple means may comprise one or more arms at the station hinged above the conveyor in such a manner that an article carried by the conveyor passes under and lifts the arms which thereby exert a force upon the article. Some of the vapor that has been contained in the article is thereby expelled, and may be sampled by a sampling probe arm at the station and the sampled vapor conveyed to a suitable vapor detector or analyzer. Because of the sensitivity of modern vapor detectors, we have discovered that an astonishingly light force expels a sufficient amount of the interior vapor to be detected. Accordingly articles that carry material giving off such vapors, unless completely airtight, are readily discovered or distinguished from other articles passing along the conveyor.

BRIEF DESCRIPTION OF THE DRAWING

The foregoing and other objects, advantages and novel features of the invention will be more fully apparent from the following description when read in connection with the accompanying drawing. The sole FIGURE of the drawing illustrates somewhat diagrammatically an embodiment of the invention in perspective view.

DESCRIPTION OF THE PREFERRED EMBODIMENT

A fexible conveyor belt 10 moves in the direction of the arrows 12. The conveyor belt is shown carrying an article, exemplified by a package 14. The package 14 may be an attache case, suitcase, or paper covered package. At the station a plurality of depressor arms 16 are hinged as on a common pin 20 to swing around the axis of the pin. A wand or arm 22 at the station has apertures 22a. The wand 22 leads through flexible tubing 24 to a vapor detector, as indicated, into which the sampled vapors mingled with the ambient atmosphere are pumped.

In operation an article such as the article 14 to be tested is placed on the conveyor. It is carried in the direction of the arrows 12 by the conveyor. As it engages the depressor arms they are swung up. The depressor arms are designed each to apply approximately 4 pounds of force on the article as it moves along the belt. The force may be as little as about 2 pounds or as great as about 20 pounds. If the arms are not heavy enough in themselves to exert that amount of force on the article, they may be weighted by additional weights such as 26 between the hinge and the distal or contact end of the arms. A minute amount of vapor is expelled by the force of the depressor arms. The expelled or emitted vapor is drawn into the wand 22 through the apertures 22a and thence through the flexible tubing 24 which leads to the vapor detector. If desired the wand 22 may be manually brought adjacent the seams or outer folds of the article under test.

Vapor detectors, particularly those which may be designed to detect low molecular weight hydrocarbons may be made extremely sensitive and may detect such small quantities as one part per million or possibly one part per billion in the vapor that is sampled. It has been found empirically that with the small forces indicated above enough vapor is expelled from the articles under test to ascertain whether or not they carry within them the material giving rise to the vapors for which the test is designed.

Sensitive detectors such as electron capture detectors are known. The tubing 24 may lead to such a detector. Alternatively, the tubing 24 may correspond to the inlet tubing of apparatus described in the copending U.S. patent application of Lerner et al, Ser. No. 779,964 filed on Mar. 22, 1977, also assigned to the U.S. Government, and which discloses method and apparatus for detecting low molecular weight hydrocarbons. The vapor detector supplies an electrical signal, ordinarily converted into a visual or audible signal. If desired, the electrical signal indicating detection of a low molecular weight hydrocarbon may be used to actuate a marking device 30 schematically shown. The marking device may include an aerosol spray or other marking means actuated to mark the article for example by a spray 32 of ink or other coloring matter, or (not shown) an armature may be provided movable in response to the signal to cause a marking pen or crayon carried by the armature to strike and mark the article. Alternatively (not illustrated) the signal may cause the article to be moved off the conveyor or conducted via a different conveyor to a different designation.

The apparatus constructed according to the invention is therefore simple, requires no vacuum chamber, requires no application of alternating pressures, permits a testing method which is rapid, simple, accurate, and non-destructive, and permits the gentle handling of the articles under inspection.

What is claimed is:

1. Apparatus for sampling vapor from articles carried by a conveyor comprising, at a station along said conveyor:
    an arm arranged to press upon an article carried past said station by said conveyor to cause a vapor to be emitted by the article, and
    a sampling probe for sampling the vapor emitted by the article when the article is pressed by said arm.

2. Apparatus as claimed in claim 1, said arm being hinged to swing from above said conveyor and thus to press upon any article passing the station at said conveyor.

3. Apparatus as claimed in claim 2, said arm being weighted between the hinge axis and a distal end arranged to contact the passing article.

4. Apparatus for sampling vapor comprising:
    a conveyor for conveying articles along a path,
    a depressor arm hinged to swing above a station on said conveyor path,
    a sampling probe at said station,
    whereby the said arm will be swung up by an article passing the station on the conveyor, the article will be compressed by the force exerted by the arm, and the probe will receive a vapor sample from the resultant compression of the article.

5. Apparatus as claimed in claim 4, said arm carrying a weight between the swing axis and the distal end of the arm.

6. Apparatus as claimed in claim 5, several arms as claimed in claim 5 being arranged to swing independently.

7. Apparatus as claimed in claim 6, said arms each exerting a weight on the article of between about 2 pounds and about 20 pounds.

8. Apparatus for securing vapor samples from articles carried by a conveyor comprising:
    a testing station along said conveyor;
    means at said station for exerting a force on an article by direct-contact mechanical means as the article passes said station on the conveyor to cause a vapor to be expelled from said article; and
    means at said station for collecting a sample of said vapor when expelled from said article by said force.

9. Apparatus claimed in claim 8 wherein said collecting means comprises a sampling probe.

10. Apparatus as claimed in claim 8, said force exerting means comprising arms for exerting force on the articles as they pass said station.

11. Apparatus as claimed in claim 8, said force being between about 2 and about 20 pounds.

12. Apparatus as claimed in claim 8, further comprising means for detecting vapors coupled to said collecting means.

13. Apparatus as claimed in claim 12 said detecting means providing an electrical signal on detection of certain vapors, said apparatus further comprising a marking device responsive to said signal for marking said article.

* * * * *